(12) United States Patent
Kikuchi et al.

(10) Patent No.: US 10,344,212 B2
(45) Date of Patent: Jul. 9, 2019

(54) LIQUID CRYSTAL DEVICE

(71) Applicants: KYUSHU UNIVERSITY, NATIONAL UNIVERSITY CORPORATION, Fukuoka (JP); JNC CORPORATION, Tokyo (JP); JNC PETROCHEMICAL CORPORATION, Tokyo (JP)

(72) Inventors: Hirotsugu Kikuchi, Fukuoka (JP); Yasushi Okumura, Fukuoka (JP); Hiroki Higuchi, Fukuoka (JP); Hiroya Nishikawa, Fukuoka (JP); Kazuya Shiroshita, Fukuoka (JP); Shinichi Yamamoto, Chiba (JP); Koki Sago, Chiba (JP); Yasuhiro Haseba, Chiba (JP)

(73) Assignees: KYUSHU UNIVERSITY, NATIONAL UNIVERSITY CORPORATION, Fukuoka (JP); JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 54 days.

(21) Appl. No.: 15/432,928

(22) Filed: Feb. 15, 2017

(65) Prior Publication Data
US 2017/0233653 A1 Aug. 17, 2017

(30) Foreign Application Priority Data

Feb. 16, 2016 (JP) ................................. 2016-026840

(51) Int. Cl.
C09K 17/34 (2006.01)
C09K 19/34 (2006.01)
C07D 319/06 (2006.01)
H01G 4/04 (2006.01)
H01G 4/14 (2006.01)

(52) U.S. Cl.
CPC ........ *C09K 19/3402* (2013.01); *C07D 319/06* (2013.01); *H01G 4/04* (2013.01); *H01G 4/14* (2013.01); *C09K 2019/3422* (2013.01); *Y10T 428/10* (2015.01)

(58) Field of Classification Search
CPC .... C09K 19/3402; C09K 19/10; C09K 19/12; C09K 19/16; C09K 19/18; C09K 19/20; C09K 2019/3422; C09K 2019/122–125; F21V 14/003; H01G 14/018; H01G 14/04; C07D 319/00
USPC ...... 428/1.1; 349/20, 182, 188, 33; 362/257; 252/299.64–299.68
See application file for complete search history.

(56) References Cited

U.S. PATENT DOCUMENTS

2015/0240159 A1* 8/2015 Yamamoto ............. C09K 19/20
349/86

FOREIGN PATENT DOCUMENTS

JP 2006155944 6/2006

* cited by examiner

*Primary Examiner* — Ruiyun Zhang
(74) *Attorney, Agent, or Firm* — JCIPRNET

(57) ABSTRACT

One aspect is contemplated for providing a device having a liquid crystal material exhibiting a dielectric constant of 1000 or more at a temperature at which a specific liquid crystal phase is developed, and a unit configured to apply voltage to the liquid crystal material at the temperature at which the specific liquid crystal phase is developed.

11 Claims, 3 Drawing Sheets

LIQUID CRYSTAL DEVICE

CROSS-REFERENCE TO RELATED APPLICATION

This application claims the benefit of and priority to Japanese Patent Application No. 2016-026840, filed on Feb. 16, 2016, the entire contents of which is incorporated herein by reference.

TECHNICAL FIELD

The invention relates to a device having a liquid crystal material exhibiting a large dielectric constant.

BACKGROUND

In connection with size reduction and achievement of a large area of an electronic device, a dielectric having a large dielectric constant and easy formability has been recently required. As the dielectric having easy formability, a dielectric made of an organic material has been known so far.

Patent literature No. 1 (JP 2006-155944 A) discloses a phenazine deuterated chloranilic acid crystal obtained by alternately arranging two or more kinds of different molecules through strong hydrogen bonds, and realizing ferroelectric phase transition by relative displacement or order-disorder between acid molecules and base molecules to exhibit a large dielectric constant of 2000 to 3000 at around room temperature.

A phenazine deuterated chloranilic acid crystal disclosed in Patent Literature No. 1 exhibits a large dielectric constant of 2000 to 3000 at around room temperature, but is not a liquid crystal material.

Under such circumstances, a device having a liquid crystal material exhibiting a large dielectric constant has been required.

SUMMARY OF THE INVENTION

The present inventors have found that a liquid crystal material developing a specific liquid crystal phase exhibits a significantly large dielectric constant at a temperature at which the specific liquid crystal phase is developed.

The invention includes aspects described below.

Item 1. A device having a liquid crystal material exhibiting a dielectric constant of 1000 or more at a temperature at which a specific liquid crystal phase is developed, and a unit configured to apply voltage to the liquid crystal material at the temperature at which the specific liquid crystal phase is developed.

Item 2. The device according to item 1, wherein a dielectric constant of the liquid crystal material at the temperature at which the specific liquid crystal phase is developed is 3000 or more.

Item 3. The device according item 1 or 2, wherein SHG light intensity of the liquid crystal material at the temperature at which the specific liquid crystal phase is developed is 2 to 10 times or more larger than SHG light intensity of the liquid crystal material at a temperature at which the liquid crystal material develops a phase different from the specific liquid crystal phase.

Item 4. The device according to item 3, wherein the phase different from the specific liquid crystal phase is a crystal phase, a nematic phase and/or an isotropic phase of the liquid crystal material.

Item 5. The device according to any one of items 1 to 4, wherein the liquid crystal material contains a compound represented by formula (1):

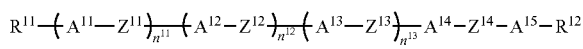

wherein, $R^{11}$ is $P^{11}$-$Sp^{11}$-, hydrogen, or alkyl having 1 to 20 carbons, arbitrary —$CH_2$— in the alkyl may be replaced by —O—, —S—, —COO—, —OCO—, —CH=CH—, —CF=CF— or —C≡C—, and arbitrary hydrogen in the alkyl may be replaced by halogen; $P^{11}$ represents a polymerizable group; $Sp^{11}$ represents a single bond or a spacer group; $R^{12}$ is $P^{12}$-$Sp^{12}$-, hydrogen, halogen, —CN, —N=C=O, —N=C=S, —$CF_3$, —$OCF_3$, or alkyl having 1 to 3 carbons, arbitrary —$CH_2$— in the alkyl may be replaced by —O—, —S—, —COO—, —OCO—, —CH=CH—, —CF=CF— or —C≡C—, arbitrary hydrogen in the alkyl may be replaced by halogen, and —$CH_3$ in the alkyl may be replaced by —CN; $P^{12}$ represents a polymerizable group; $Sp^{12}$ represents a single bond or a spacer group; $A^{11}$ to $A^{15}$ are independently a five-membered ring to an eight-membered ring, or a condensed ring having 9 or more carbons, arbitrary hydrogen of the rings may be replaced by halogen, alkyl having 1 to 5 carbons or alkyl halide, arbitrary —$CH_2$— of the alkyl having 1 to 5 carbons or the alkyl halide may be replaced by —O—, —S— or —NH—, —$CH_2$— of the rings may be replaced by —O—, —S— or —NH—, and —CH= of the rings may be replaced by —N=; $Z^{11}$ to $Z^{14}$ are independently a single bond or alkylene having 1 to 8 carbons, arbitrary —$CH_2$— in the alkylene may be replaced by —O—, —S—, —COO—, —OCO—, —CSO—, —OCS—, —N=N—, —CH=N—, —N=CH—, —N(O)=N—, —N=N(O)—, —CH=CH—, —CF=CF— or —C≡C—, and arbitrary hydrogen of the alkylene may be replaced by halogen; and $n^{11}$ to $n^{13}$ are independently 0 or 1.

Item 6. The device according to item 5, wherein, in formula (1), a sum of $n^{11}+n^{12}+n^{13}$ is 2 or 3, $A^{11}$ to $A^{14}$ are selected from the group of (A-1) to (A-5) described below, $A^{15}$ is selected from the group of (A-1) to (A-3), and further, a total of halogen atoms in $A^{11}$ to $A^{15}$ is 6 or more:

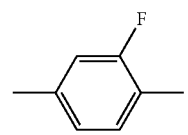

(A-1)

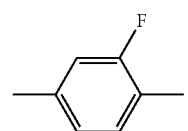

(A-2)

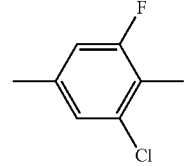

(A-3)

-continued

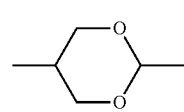
(A-4)

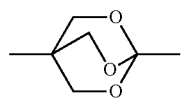
(A-5)

Item 7. The device according to item 5 or 6, wherein the liquid crystal material contains at least one compound selected from the group of compounds represented by formulas (2) and (3) described below:

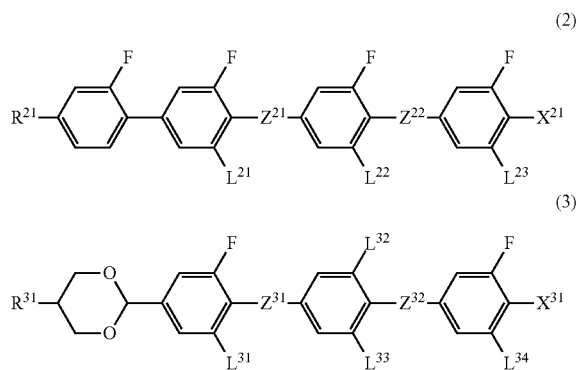

wherein, in formula (2), $R^{21}$ is alkyl having 1 to 12 carbons, alkenyl having 2 to 12 carbons or alkoxy having 1 to 11 carbons, $Z^{21}$ and $Z^{22}$ are independently a single bond, —COO— or —CF$_2$O—, $X^{21}$ is fluorine, chlorine, —CF$_3$ or —OCF$_3$, and $L^{21}$ to $L^{23}$ are independently hydrogen or fluorine, and in formula (3), $R^{31}$ is alkyl having 1 to 12 carbons or alkoxyalkyl having 1 to 11 carbons, $Z^{31}$ and $Z^{32}$ are independently a single bond, —COO— or —CF$_2$O—, $X^{31}$ is fluorine, chlorine, —CF$_3$ or —OCF$_3$, and $L^{31}$ to $L^{34}$ are independently hydrogen or fluorine.

Item 8. The device according to any one of items 1 to 7, wherein the device is a capacitor.

Item 9. A wavelength conversion device, having a liquid crystal material exhibiting a dielectric constant of 1000 or more at a temperature at which a specific liquid crystal phase is developed, and a unit configured to irradiate the liquid crystal material with light at the temperature at which the specific liquid crystal phase is developed.

Item 10. The device according to any one of items 1 to 9, wherein the liquid crystal material has positive dielectric anisotropy in the specific liquid crystal phase.

A liquid crystal material used in a device according to one aspect of the invention develops a specific liquid crystal phase and exhibits a large dielectric constant of 1000 or more at a temperature at which the specific crystal phase is developed.

The liquid crystal material used in the device according to one aspect of the invention is relatively moderate in temperature dependence of the dielectric constant, and exhibits the large dielectric constant over a wide temperature range. The liquid crystal material used in the device according to one aspect of the invention is excellent in formability. The liquid crystal material used in the device according to one aspect of the invention exhibits surprising properties in which a relaxation frequency in the specific liquid crystal phase exists in a high frequency region in comparison with a relaxation frequency in a liquid crystal phase to be developed on a higher temperature side in comparison with the specific liquid crystal phase.

DETAILED DESCRIPTION OF THE INVENTION

Figure 1:
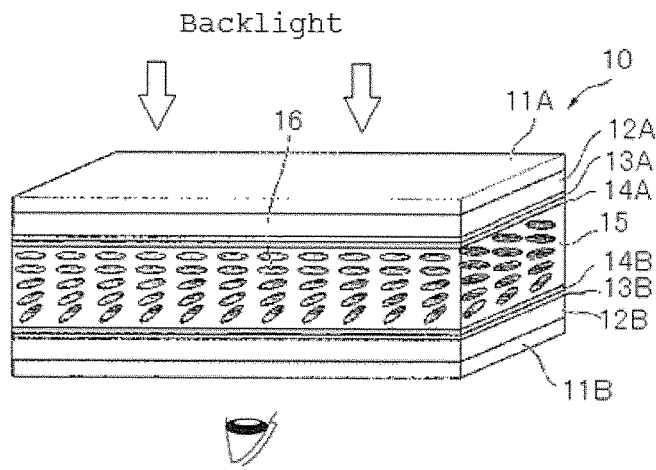
FIG. 1 is a schematic diagram of a device according to one aspect of the invention.

In the present specification, "liquid crystal compound" represents an organic compound having a mesogen moiety (mesogen), and is not limited to an organic compound that develops a liquid crystal phase. Specifically, "liquid crystal compound" is a generic term for the organic compound that develops the liquid crystal phase such as a nematic phase and a smectic phase, and an organic compound having no liquid crystal phase but being useful as a component of a liquid crystal composition.

"Liquid crystal medium" is a generic term for a composition developing the liquid crystal phase, or a composite between the composition and other materials.

"Liquid crystal material" is a generic term for the liquid crystal compound and the liquid crystal medium.

"Specific liquid crystal phase" means a phase in which SHG (second harmonic generation) light intensity is significantly larger in comparison with other phases (for example, a crystal phase, a nematic phase or an isotropic phase) of the same liquid crystal material, or other general liquid crystal materials such as 5CB (4-pentyl-4'-cyanobiphenyl). In the phase, the liquid crystal material exhibits a significantly large dielectric constant, in which temperature characteristics of a dielectric constant also become moderate. "Specific liquid crystal phase" herein is referred to as "Sandy phase" in several cases. A term "Sandy phase" is a coined word named in view of a characteristic polarization microscope image thereof. In the specific liquid crystal phase (Sandy phase), SHG light with high intensity can be specifically observed.

"Device" means a device having the liquid crystal material. "Device" also includes a device having a liquid crystal material exhibiting a dielectric constant of 1000 or more at a temperature at which the specific liquid crystal phase is developed, and the device further having a unit conjured to apply voltage to the liquid crystal material at the temperature at which the liquid crystal material develops the specific liquid crystal phase. "Device" is referred to as "liquid crystal device" in several cases.

"Dielectric constant" represents a dimensionless relative dielectric constant.

"Liquid crystal compound," "liquid crystal composition" and "liquid crystal device" herein are abbreviated as "compound," "composition" and "device," respectively, in several cases. An upper limit of a temperature range of the liquid crystal phase is a phase transition temperature between the liquid crystal phase and the isotropic phase, and "phase transition temperature" is abbreviated simply as "clearing point" or "maximum temperature" in several cases. A lower limit of the temperature range of the liquid crystal phase is abbreviated simply as "minimum temperature" in several cases.

Unless otherwise noted, an amount of compound expressed in terms of a percentage herein means a percentage by weight (% by weight) based on the total weight of the composition.

"Alkyl" herein may be linear or branched, and specific examples include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, —$C_{10}H_{21}$, —$C_{11}H_{23}$ or —$C_{12}H_{25}$. Specific examples of "alkyl" include —$C_{13}H_{27}$, —$C_{14}H_{29}$, —$C_{15}H_{31}$, —$C_{16}H_{33}$, $C_{17}H_{35}$, —$C_{18}H_{37}$, —$C_{19}H_{39}$ or —$C_{20}H_{41}$.

"Alkenyl" herein may be linear or branched, and specific examples include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=$CHC_3H_7$, —$CH_2$CH=$CHC_2H_5$, —$(CH_2)_2$—CH=$CHCH_3$ or —$(CH_2)_3$—CH=$CH_2$. Specific examples of "alkenyl" include —$(CH_2)_4$—CH=$CH_2$, —$(CH_2)_5$—CH=$CH_2$, —$(CH_2)_6$—CH=$CH_2$, —$(CH_2)_7$—CH=$CH_2$, —$(CH_2)_8$—CH=$CH_2$, —$(CH_2)_9$—CH=$CH_2$ or —$(CH_2)_{10}$—CH=$CH_2$.

"Alkynyl" herein may be linear or branched, and specific examples include —C≡CH, —C≡$CCH_3$, —$CH_2$C≡CH, —C≡$CC_2H_5$, —$CH_2$C≡$CCH_3$, —$(CH_2)_2$—C≡CH, —C≡$CC_3H_7$, —$CH_2$C≡$CC_2H_5$, —$(CH_2)_2$—C≡$CCH_3$ or —C≡$C(CH_2)$.

"Alkoxy" herein may be linear or branched, and specific examples include —$OCH_3$, —$OC_2H_5$, —$OC_3H_7$, —$OC_4H_9$, —$OC_5H_{11}$, —$OC_6H_{13}$, —$OC_7H_{15}$, $OC_8H_{17}$, —$OC_9H_{19}$, —$OC_{10}H_{21}$ or —$OC_{11}H_{23}$.

"Alkoxyalkyl" herein may be linear or branched, and specific examples include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ or —$(CH_2)_5$—$OCH_3$. Specific examples of "alkoxyalkyl" include —$(CH_2)_6$—$OCH_3$, —$(CH_2)_7$—$OCH_3$, —$(CH_2)_8$—$OCH_3$, —$(CH_2)_9$—$OCH_3$ or —$(CH_2)_{10}$—$OCH_3$.

"Alkenyloxy" herein may be linear or branched, and specific examples include —$OCH_2$CH=$CH_2$, —$OCH_2$CH=$CHCH_3$ or —$OCH_2$CH=$CHC_2H_5$.

Specific example of "halogen" herein include fluorine, chlorine, bromine or iodine.

Specific examples of "polymerizable group" herein include an acrylic group, a methacrylic group, a vinyloxy group, an isocyanate group, an isothiocyanate group, an epoxy group, an aziridine group, an azlactone group, a chloro-s-triazine group or β-chloroethylaminosulfonyl group, but are not limited thereto.

Specific examples of "spacer group" herein include —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, or —$C_{10}H_{20}$—, or a group in which one or more pieces of $CH_2$ of the groups are replaced by oxygen or COO, but are not limited thereto. However, a case where oxygen atoms are adjacent to each other is excluded.

The liquid crystal material used in the device according to one aspect of the invention provides one or more features described below.

(a) The liquid crystal material exhibits a large dielectric constant of 1000 or more at the temperature at which the specific liquid crystal phase is developed in a wide range of frequency (i.e., measured frequency) of alternating-current voltage applied to the liquid crystal material, and a large dielectric constant of maximum of 10000 or more.

(b) The liquid crystal material exhibits a large dielectric constant of 1000 or more from room temperature to 150° C., preferably from 40 to 120° C., and further preferably in the wide temperature range in which the specific liquid crystal phase is developed.

(c) A relaxation frequency in the specific liquid crystal phase on a low temperature side exists in a high frequency region, in comparison with a relaxation frequency in the nematic phase which is developed on a higher temperature side in comparison with the specific liquid crystal phase. In general, a frequency to which the material can respond is reduced by increasing of viscosity at a low temperature in an ordinary liquid crystal material, and therefore the relaxation frequency on the low temperature side is lower than a relaxation frequency on a high temperature side.

(d) The liquid crystal material provides high positive dielectric anisotropy $\Delta\varepsilon$ ($\varepsilon_{para}-\varepsilon_{perp}$) in a state in which the specific liquid crystal phase is developed.

The liquid crystal material used in the device according to one aspect of the invention develops SHG in a bulk (i.e., body part not in contact with an interface) in several cases. In taking into account conditions necessary for developing SHG being asymmetry of a system, the liquid crystal material that develops SHG in several cases has asymmetry in the specific liquid crystal phase in several cases. Therefore, in comparison with the general liquid crystal material, the liquid crystal material used in the device according to one aspect of the invention has a larger amount of parallel aggregation of molecules (i.e., state in which directions of dipole moments of the molecules are arranged in a substantially same direction and the molecules are aggregated) also in the bulk in the specific liquid crystal phase. As a result, a significant large dielectric constant is assumed to be developed.

Hereinafter, the liquid crystal material and the device having the liquid crystal material according to one aspect of the invention will be described in more detail with reference to drawings.

1. Liquid Crystal Material

A liquid crystal material used in the device according to one aspect of the invention is the liquid crystal material developing the specific liquid crystal phase, in which a value of dielectric constant is 1000 or more at the temperature at which the specific liquid crystal phase is developed. The liquid crystal material used in the device according to one aspect of the invention contains a compound represented by formula (1) described below, and preferably in an amount of 60% by weight or more, and further preferably 80% by weight or more.

Formula 1

(1)

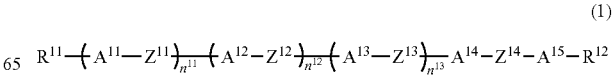

In formula (1), $R^{11}$ is $P^{11}$-$Sp^{11}$-, hydrogen or alkyl having 1 to 20 carbons, arbitrary —$CH_2$— in the alkyl may be replaced by —O—, —S—, —COO—, —OCO—, —CH═CH—, —CF═CF— or —C≡C—, and arbitrary hydrogen in the alkyl group may be replaced by halogen. Here, $P^{11}$ represents a polymerizable group and $Sp^{11}$ represents a single bond or a spacer group. $R^{11}$ is, preferably, alkyl having 1 to 7 carbons, arbitrary —$CH_2$— in the alkyl may be replaced by —O—, —CH═CH— or —C≡C—, and arbitrary hydrogen of the alkyl group may be replaced by halogen.

$R^{12}$ is $P^{12}$-$Sp^{12}$-, hydrogen, halogen, —CN, —N═C═O, —N═C═S, —$CF_3$, —$OCF_3$ or alkyl having 1 to 3 carbons, arbitrary —$CH_2$— in the alkyl may be replaced by —O—, —S—, —COO—, —OCO—, —CH═CH—, —CF═CF— or —C≡C—, arbitrary hydrogen in the alkyl may be replaced by halogen, and —$CH_3$ in the alkyl may be replaced by —CN. Here, $P^{12}$ represents a polymerizable group and $Sp^{12}$ represents a single bond or a spacer group. $R^{12}$ is, preferably, halogen, —CN, —N═C═S, —$CF_3$, —$OCF_3$ or alkyl having 1 to 3 carbons, and arbitrary hydrogen of the alkyl may be replaced by halogen.

$A^{11}$ to $A^{15}$ are independently a five-membered ring to an eight-membered ring, or a condensed ring having 9 or more carbons, arbitrary hydrogen of the rings may be replaced by halogen, or alkyl having 1 to 5 carbons or alkyl halide. Arbitrary —$CH_2$— of alkyl having 1 to 5 carbons or alkyl halide may be replaced by —O—, —S— or —NH—, —$CH_2$— of the rings may be replaced by —O—, —S— or —NH—, and —CH═ of the rings may be replaced by —N═. $A^{11}$ to $A^{14}$ are, preferably, a ring selected from the group of (A-1) to (A-5) described below, and $A^{15}$ is a ring selected from the group of (A-1) to (A-3) described below.

Formula 2

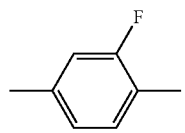
(A-1)

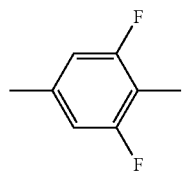
(A-2)

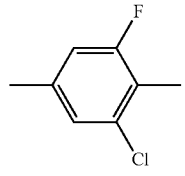
(A-3)

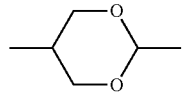
(A-4)

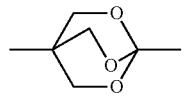
(A-5)

$Z^{11}$ to $Z^{14}$ are independently a single bond or alkylene having 1 to 8 carbons, arbitrary —$CH_2$— in the alkylene may be replaced by —O—, —S—, —COO—, —OCO—, —CSO—, —OCS—, —N═N—, —CH═N—, —N═CH—, —N(O)═N—, —N═N(O)—, —CH═CH—, —CF═CF— or —C≡C—, and arbitrary hydrogen may be replaced by halogen. $Z^{11}$ to $Z^{14}$ are, preferably, independently a single bond, —COO— or —$CF_2O$—. At least one piece of $Z^{11}$ to $Z^{14}$ is further preferably —COO— or —$CF_2O$—.

$n^{11}$ to $n^{13}$ are independently 0 or 1, and preferably a sum ($n^{11}$+$n^{12}$+$n^{13}$) of $n^{11}$ to $n^{13}$ is 2 or 3.

The liquid crystal material used in the device according to one aspect of the invention contains a compound represented by formula (1) described below in an amount of preferably 60% by weight or more, and further preferably 80% by weight or more.

Formula 3

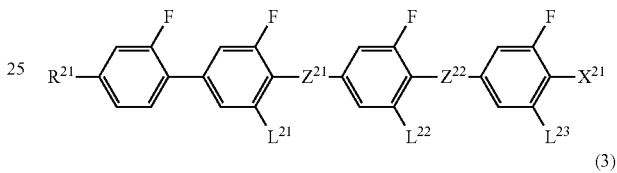
(2)

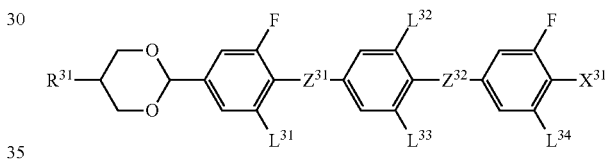
(3)

In formula (2), $R^{21}$ is alkyl having 1 to 12 carbons, alkenyl having 2 to 12 carbons or alkoxy having 1 to 11 carbons. $Z^{21}$ and $Z^{22}$ are independently a single bond, —COO— or —$CF_2O$—, $X^{21}$ is fluorine, chlorine, —$CF_3$ or —$OCF_3$, and $L^{21}$ to $L^{23}$ are independently hydrogen or fluorine. In formula (3), $R^{31}$ is alkyl having 1 to 12 carbons, or alkoxy alkyl having 1 to 11 carbons, $Z^{31}$ and $Z^{32}$ are independently a single bond, —COO— or —$CF_2O$—, $X^{31}$ is fluorine, chlorine, —$CF_3$ or —$OCF_3$, and $L^{31}$ to $L^{34}$ are independently hydrogen or fluorine.

The liquid crystal material used in the device according to one aspect of the invention may contain a polymer having no mesogen and/or a polymer having a mesogen. As the polymer having the mesogen, the liquid crystal material may contain a polymer formed by polymerization of a compound represented by formula (1) having a $P^{11}$-$Sp^{11}$-, at a terminal as $R^{11}$. The polymerizable group $P^{11}$ is an acrylic group, a methacrylic group, a vinyl group, an isocyanate group, an isothiocyanate group, an epoxy group, an aziridine group, or an azlactone group, for example. The polymer may contain a polymerization initiator, a curing agent, a catalyst, a stabilizer, a dichroic dye or a photochromic compound within the range in which an effect of the liquid crystal material is not adversely affected.

A plastic member having properties (large dielectric constant or the like) of the liquid crystal material can be formed by using a compound containing the polymerizable group, or another polymerizable compound, and can be applied as a dielectric to be arranged between electrodes of a capacitor, a piezoelectric element or a nonlinear optical element. Use of a glass substrate for gripping a liquid crystal layer can also be omitted by using the plastic member containing the polymer of the liquid crystal material as a liquid crystal layer of a liquid crystal display device, and consequently manufacturing cost can be significantly reduced.

The liquid crystal material used in the device according to one aspect of the invention may be a composite material between at least one kind of compound represented by formulas (1) to (3) described above, and a polymer compound, and for example, a polymer network may be formed within the liquid crystal material.

2. Device

A device according to one aspect of the invention is a device having a liquid crystal material developing the specific liquid crystal phase, and the liquid crystal material exhibiting a dielectric constant of 1000 or more at the temperature at which the specific liquid crystal phase is developed. The device according to one aspect of the invention has a unit configured to apply voltage to the liquid crystal material at the temperature at which the liquid crystal material containing at least one compound represented by formulas (1) to (3) develops the specific liquid crystal phase. The unit may be a unit other than the liquid crystal layer of the liquid crystal display device or a unit other than the dielectric of the capacitor, for example. For example, the device as a liquid crystal display device includes the liquid crystal material as a liquid crystal layer and a unit configured to apply voltage to the liquid crystal material, where the unit includes two transparent electrodes configured to apply voltage to the liquid crystal material arranged therebetween, and also the unit may further include an alignment film, a color filter, a grass substrate, and/or a polarizing filter. For example, the device as a capacitor includes the liquid crystal material as a dielectric and a unit configured to apply voltage to the liquid crystal material, where the unit includes two electrodes configured to apply voltage to the liquid crystal material arranged therebetween. The device may be formed so as to have the liquid crystal material, and a unit configured to irradiate the liquid crystal material with light at the temperature at which the specific liquid crystal phase is developed. For example, the unit may be a laser light source for developing a nonlinear optical effect of the liquid crystal material.

The device may be formed so as to apply voltage to the liquid crystal material in a state in which the liquid crystal material develops a phase other than the specific liquid crystal phase.

The device according to one aspect of the invention is liquid crystal display device 10 having the liquid crystal material. FIG. 1 is a schematic configuration diagram of a part of liquid crystal display device 10. Liquid crystal display device 10 has first polarizing filter 11A, first glass substrate 12A, first transparent electrode 13A, first alignment film 14A, liquid crystal layer 15, second alignment film 14B, second transparent electrode 13B, second glass substrate 12B and second polarizing filter 11B. Directions of polarization of first polarizing filter 11A and second polarizing filter 11B are provided so as to be perpendicular to each other, and liquid crystal layer 15 includes liquid crystal material 16 described above. First transparent electrode 13A and second transparent electrode 13B are made of a transparent material such as ITO. Twisting is generated in liquid crystal material 16 in liquid crystal layer 15 by first alignment film 14A and second alignment film 14B. A color filter layer of RGB (or RGBY) may be provided between second transparent electrode 13B and second glass substrate 12B in such a manner that liquid crystal display device 10 can display a color image. A configuration in which liquid crystal display device 10 applies a liquid crystal drive system having a TN (twisted nematic) mode is described, but liquid crystal display device 10 may apply a liquid crystal drive system having a VA (vertical alignment) mode or an IPS (in-plane switching) mode.

In general, a temperature inside the liquid crystal display device during operation is higher than room temperature. Liquid crystal material 16 included in liquid crystal layer 15 in an operating temperature region develops the specific liquid crystal phase and exhibits large dielectric anisotropy $\Delta\varepsilon$. Therefore, in the operating temperature region, refractive index anisotropy of liquid crystal layer 15 increases, and the direction of polarization of light can be significantly varied. Accordingly, linearly polarized light entering the liquid crystal layer 15 from a backlight through first polarizing filter 11A is, while the light propagates in a thickness direction of liquid crystal layer 15, varied in a polarization state according to elimination of twisting of liquid crystal material 16 exhibiting high refractive index anisotropy, and is emitted from second polarization filter 11B, or blocked by second polarizing filter 11B. Elimination of twisting of liquid crystal material 16 is controlled according to voltage applied through first transparent electrode 13A and second transparent electrode 13B.

The device according to one aspect of the invention is a capacitor having the liquid crystal material or a polymer thereof as the dielectric between the electrodes. The liquid crystal material exhibits a large dielectric constant of 1000 or more (maximum of 10000 or more) in a wide range of temperature and frequency. Therefore, the capacitor can hold a large capacity of electric charge, and enables a high-speed response (charging and discharging). The device according to one aspect of the invention is a capacitor (for example, an on-board capacitor) having the liquid crystal material (for example, compound DIO-3 to be described later) that develops the specific liquid crystal phase on a relatively high temperature side (40° C. or higher).

The device according to one aspect of the invention is a piezoelectric device having the liquid crystal material or the polymer thereof as a piezoelectric material between the electrodes. For example, the device as a piezoelectric device includes the liquid crystal material (or the polymer thereof) as a piezoelectric material and a unit configured to apply voltage to the liquid crystal material, where the unit includes two electrodes configured to apply voltage to the liquid crystal material arranged therebetween to actuate the device. The device according to one aspect of the invention is a secondary battery containing the liquid crystal material in an electrolyte.

The device according to one aspect of the invention is a device having a unit configured to irradiate the liquid crystal material with light from a laser or the like at the temperature at which at least the specific liquid crystal phase is developed. The liquid crystal material develops SHG, and therefore the device according to one aspect of the invention is a nonlinear optical device in which wavelength conversion can be made.

The device according to one aspect of the invention may be further provided with a temperature control means (e.g., a heating device and/or a cooling device) for heating or cooling the liquid crystal material to the temperature at which the specific crystal phase is developed.

EXAMPLES

Hereinafter, the invention will be described in more detail by way of examples, but the invention is not limited to the examples. Unless otherwise mentioned, "%" means "% by weight."

Example 1 (Phase Transition Temperature of Compound DIO-3)

In the present Example and Examples described below, compound DIO-3 represented by formula (4) described below was used as a liquid crystal material, in which $R^{31}$ of a compound represented by formula (3) described above is an alkyl group having 3 carbons, $L^{33}$ is hydrogen, $Z^{32}$ is a single bond, and $L^{31}$, $L^{32}$, $L^{34}$, and $X^{31}$ are fluorine, and $Z^{31}$ is —COO—.

Formula 4

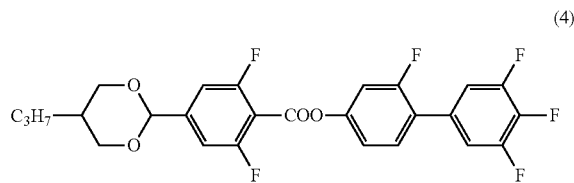

(4)

Figure 2:
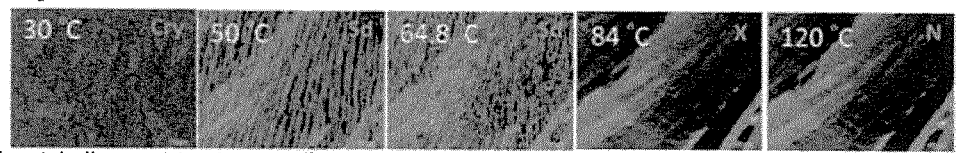
FIG. 2 shows POM (polarized light microscopy) images of the liquid crystal material to be used in the device according to the aspect of the invention.
Figure 2:
Figure 2:
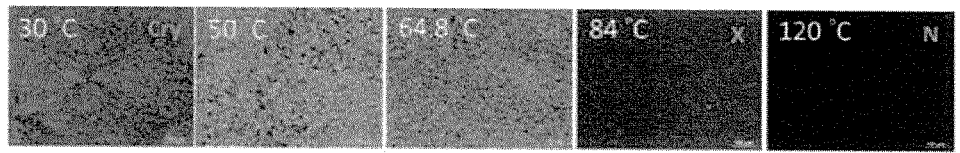

Three kinds of cells, including a non-alignment treatment cell, a horizontal alignment treatment cell and a vertical alignment treatment cell were used, and a phase transition temperature of the compound DIO-3 was identified using a polarizing microscope and DSC (Differential Scanning calorimeter DSC1, made by METTLER-TOLEDO LLC). As measurement conditions of DSC, a heating and cooling rate is 5° C./min (polarized light microscopy (POM) image in FIG. 2). In FIG. 2, an upper row shows polarized microscope images formed by using the non-alignment treatment cell, a middle row shows polarized microscope images formed by using the horizontal alignment treatment cell, and a lower row shows polarized microscope images formed by using the vertical alignment treatment cell. As legends in FIG. 2, Cry represents a crystal phase, Sd represents a Sandy phase, X represents an unknown phase, and N represents a nematic phase. From the measurement results, a phase transition temperature of the compound DIO-3 was as shown in Table 1 below.

TABLE 1

|  |  | Crystal phase | Sandy phase | Unknown phase | Nematic phase | Isotropic phase |
|---|---|---|---|---|---|---|
| Temperature rise | room temperature to 44.1° C. | 44.1 to 69.0° C. | 69.0 to 96.6° C. | 96.6 to 175° C. | 175° C. or higher |
| Temperature fall | room temperature to 30.0° C. | 30.0 to 67.0° C. | 67.0 to 84.0° C. | 84.0 to 174° C. | 174° C. or higher |

In the Table, "Sandy phase" represents the specific liquid crystal phase. Difference of a lower limit temperature (44.1° C.) at which the Sandy phase is developed during temperature rise from a lower limit temperature (30.0° C.) at which the Sandy phase is developed during temperature fall is considered to be caused by an influence of measurement conditions, for example, crystallization, by impurities contained in the liquid crystal material, or structure of the cell.

Example 2 (Dielectric Relaxation of Compound DIO-3)

Figure 3:
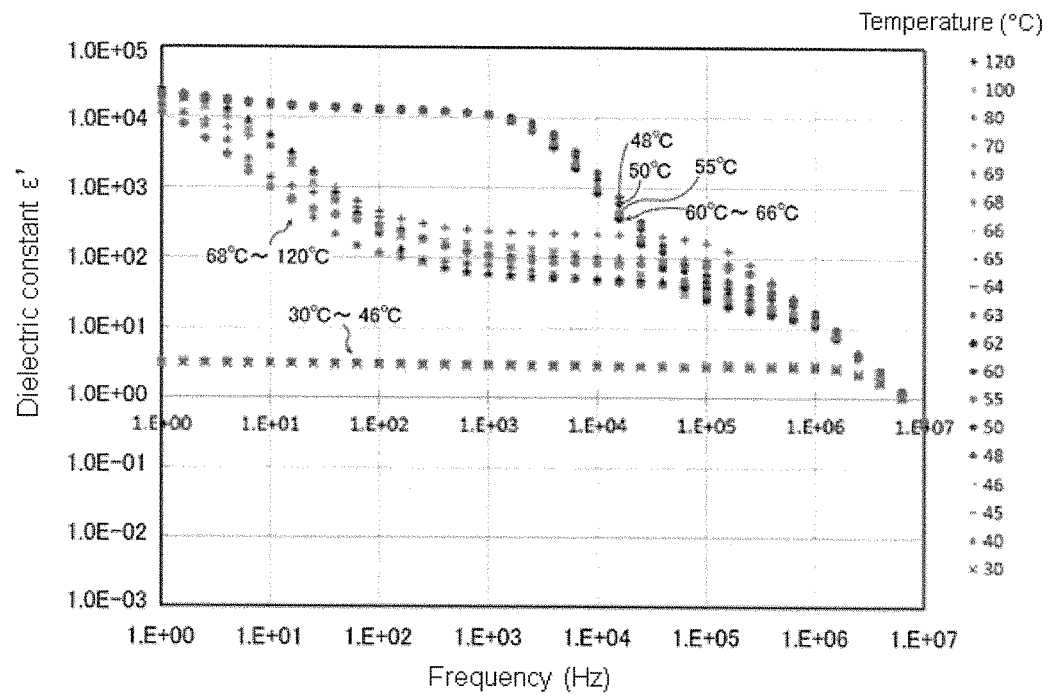
FIG. 3 is a diagram showing a dielectric relaxation spectrum of the liquid crystal material used in the device according to the aspect of the invention.

In the present Example, a dielectric relaxation spectrum of the compound DIO-3 was measured. Measurement was carried out by using 126096 W Dielectric Measurement System (made by Toyo Corporation) as a measuring device, and applying a sine wave at 0.1 V, while temperature was decreased. After the temperature reached a desired temperature, the temperature was maintained at the level for 5 min, and then the measurement was started. A cell used is a vertical alignment cell made by EHC Co., Ltd., and a cell gap is 10 micrometers. The results are shown in FIG. 3. In FIG. 3, a vertical axis represents a dielectric constant $\varepsilon'$ in the range of $10^{-3}$ (1.0E-03) to $10^5$ (1.0E+05). A horizontal axis represents a frequency (i.e., measured frequency) (Hz) of alternating-current voltage applied in the range of 1 Hz (1.E+00) to $10^7$ Hz (1.E+07). Numbers (30 to 120) in legends each represent a measured temperature (° C.).

In the temperature range of 48° C. to 66° C. in the temperature range in which the Sandy phase is developed, a significantly large dielectric constant of 10000 is exhibited in 1 Hz (1.E+00) to 1 KHz (1.E+03), and the dielectric constant is moderately reduced on a high frequency side from 1 KHz, but a large dielectric constant of 1000 is exhibited also in 10 KHz (1.E+04). In the temperature range (48° C. to 66° C.), each plot corresponding to each temperature is overlapped particularly in the range of 1 Hz (1.E+00) to 10 KHz (1.E+04), and temperature dependence of the dielectric constant was known to be small.

Example 3 (SHG Spectrum of Compound DIO-3)

Figure 4:
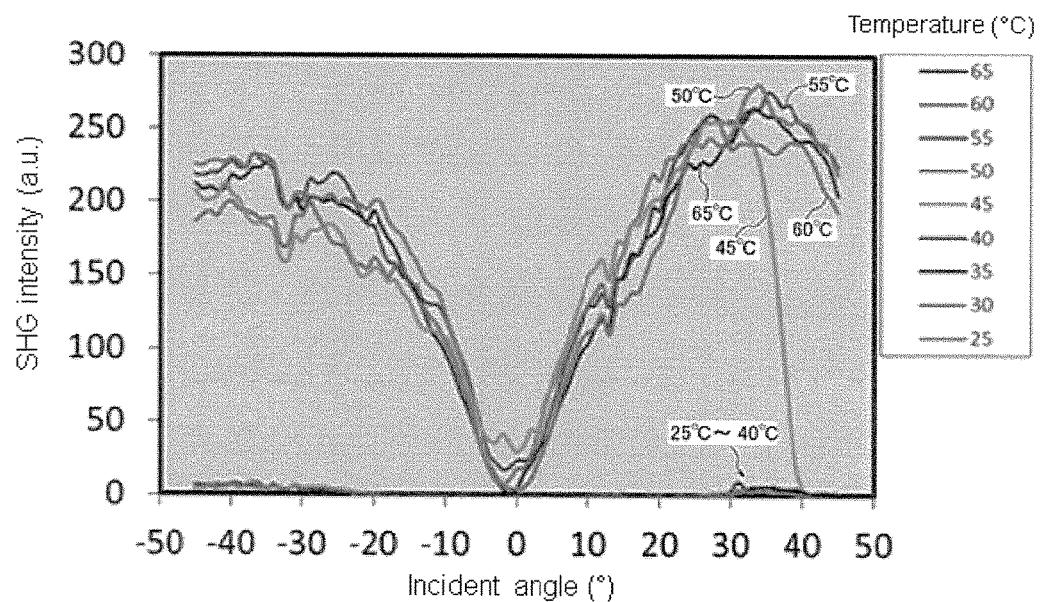
FIG. 4 is a diagram showing an SHG light intensity spectrum of the liquid crystal material to be used in the device according to the aspect of the invention.

In the present Example, measurement was carried out on an SHG spectrum of compound DIO-3 during homeotropic alignment (application of 7 V) (polarization condition p-p). A measuring device is a nonlinear optical material evaluation system made by Tokyo Instruments Inc., and a cell used is a vertical alignment cell (cell gap 10 micrometers) made by EHC Co., Ltd. The results are shown in FIG. 4. In FIG. 4, a vertical axis represents SHG intensity (in an arbitrary unit (a.u.)), a horizontal axis represents an incident angle)(° of a laser beam in the range of −50° to 50°, and numbers (25 to 65) in legends each represent a measured temperature (° C.).

As shown in FIG. 4, in the temperature range of 45° C. to 65° C. within the temperature range in which the Sandy phase is developed, significantly high SHG intensity was exhibited. In particular, in comparison of SHG intensity at an incident angle of 30°, for example, the SHG intensity in the temperature range (45° C. to 65° C.) showed values higher by 2 to 10 times than the SHG strength in the temperature range (25° C. to 40° C.) in which a crystal phase is developed. More specifically, presence of parallel aggregation of molecules of compound DIO-3 is strongly suggested in the Sandy phase.

Figure 5:
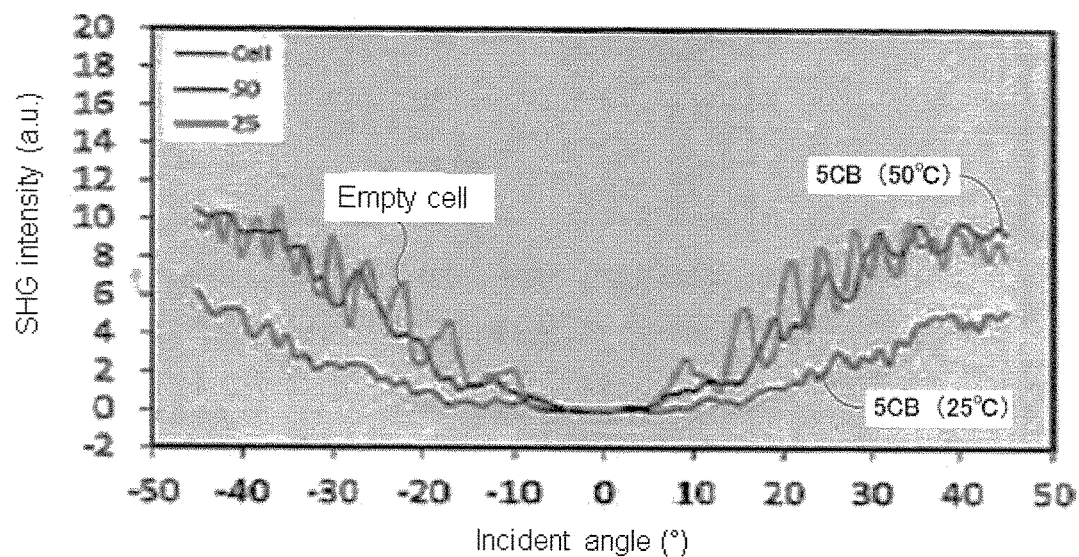
FIG. 5 is a diagram showing an SHG light intensity spectrum of a conventional organic material.

As Comparative Example, FIG. 5 shows an SHG spectrum of an empty cell of the vertical alignment treatment cell made by EHC Co., Ltd., and an SHG spectrum of 5CB (i.e., 4-pentyl-4'-cyanobiphenyl) being a conventional liquid crystal material sealed into the empty cell. Measurement was carried out under the same measurement conditions and using the device from which the data in FIG. 4 was collected. In FIG. 5, a vertical axis represents SHG intensity (in an arbitrary unit (a.u.)), a horizontal axis represents an incident angle) (°) of a laser beam in the range of −50° to 50°, and numbers 50 and 25 in legends each represent a measured temperature (° C.). As shown in FIG. 5, in comparison of SHG intensity at an incident angle of 30°, for example, the SHG intensity of compound DIO-3 (about 250) is found to be significantly larger than the SHG intensity (about 10 or less at both of 25° C. and 50° C.) of 5CB.

Example 4 (SHG Spectrum of Compound DIO-3)

Figure 6:
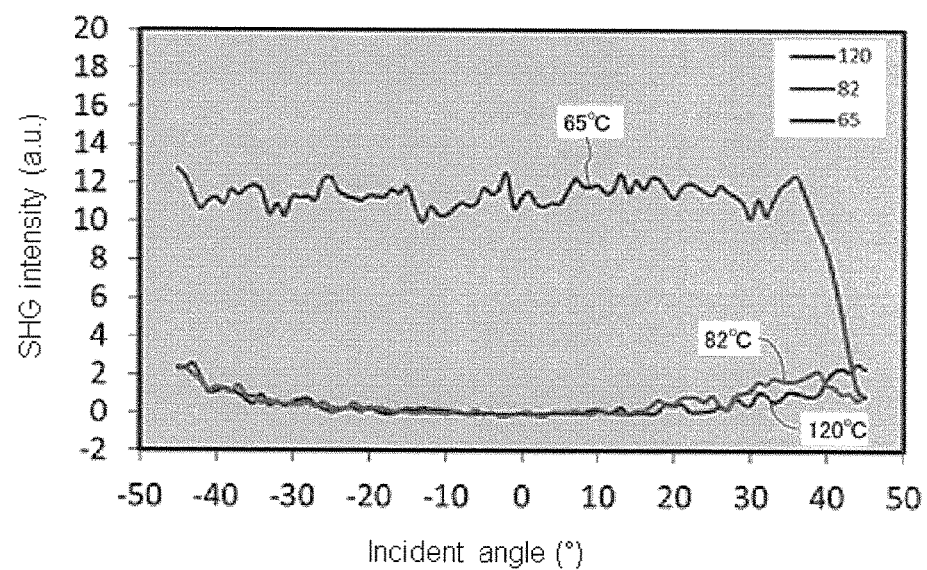
FIG. 6 is a diagram showing an SHG light intensity spectrum of the liquid crystal material to be used in the device according to the aspect of the invention.

In the present Example, measurement was carried out on an SHG spectrum of compound DIO-3 during substantially random alignment. A measuring device is a nonlinear optical material evaluation system made by Tokyo Instruments Inc., and a cell used is a vertical alignment cell (cell gap 10 micrometers) made by EHC Co., Ltd. The results are shown in FIG. 6. Numbers 65 to 120 in legends in FIG. 6 each represent a measured temperature (° C.).

A reason which the SHG spectrum at 65° C. as shown in FIG. 4 in Example 3 is significantly different from the SHG spectrum at 65° C. in FIG. 6 is considered that compound DIO-3 is not vertically aligned in the Sandy phase to take substantially random alignment by no voltage application as in the present Example. As shown in FIG. 6, from the results in which the SHG spectrum at 65° C. in which the Sandy phase is developed takes a value larger than the value of the SHG spectrum on a high temperature side (82° C., 120° C.) not in the Sandy phase, presence of parallel aggregation is strongly suggested within bulk, not on an interface. Moreover, the SHG light intensity is found to specifically become strong in the Sandy phase.

What is claimed is:

1. A device, comprising:
   a liquid crystal material exhibiting a dielectric constant of 1000 or more at a temperature at which a specific liquid crystal phase is developed; and
   a unit configured to apply voltage to the liquid crystal material at the temperature at which the specific liquid crystal phase is developed,
   wherein the specific liquid phase is a phase on which second harmonic generation light with high intensity is observed, and
   the liquid crystal material comprises 80% by weight or more, based on a weight of the liquid crystal material, of a compound represented by formula (3) described below:

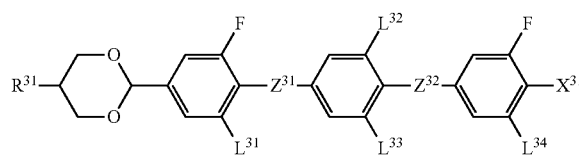

wherein in formula (3), $R^{31}$ is alkyl having 1 to 12 carbons or alkoxyalkyl having 1 to 11 carbon, $Z^{31}$ and $Z^{32}$ are independently a single bond, —COO— or —CF$_2$O—, $X^{31}$ is independently fluorine, chlorine, —CF$_3$ or —OCF$_3$, and $L^{31}$ to $L^{34}$ are independently hydrogen or fluorine.

2. The device according to claim 1, wherein a dielectric constant of the liquid crystal material at the temperature at which the specific liquid crystal phase is developed is 3000 or more.

3. The device according claim 1, wherein second harmonic generation light intensity at an incident angle of 30° of the liquid crystal material at the temperature at which the specific liquid crystal phase is developed is 2 to 10 times or more larger than second harmonic generation light intensity at an incident angle of 30° of the liquid crystal material at a temperature at which the liquid crystal material develops a phase different from the specific liquid crystal phase.

4. The device according to claim 3, wherein the phase different from the specific liquid crystal phase is a crystal phase, a nematic phase or an isotropic phase of the liquid crystal material.

5. The device according to claim 1, wherein the device is a capacitor.

6. A wavelength conversion device, comprising:
   a liquid crystal material exhibiting a dielectric constant of 1000 or more at a temperature at which a specific liquid crystal phase is developed; and
   a unit configured to irradiate the liquid crystal material with light at the temperature at which the specific liquid crystal phase is developed,
   wherein the specific liquid phase is a phase on which second harmonic generation light with high intensity is observed, and
   the liquid crystal material comprises 80% by weight or more, based on a weight of the liquid crystal material, of a compound represented by formula (3) described below:

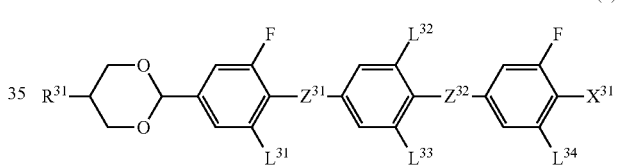

wherein in formula (3), $R^{31}$ is alkyl having 1 to 12 carbons or alkoxyalkyl having 1 to 11 carbon, $Z^{31}$ and $Z^{32}$ are independently a single bond, —COO— or —CF$_2$O—, $X^{31}$ is independently fluorine, chlorine, —CF$_3$ or —OCF$_3$, and $L^{31}$ to $L^{34}$ are independently hydrogen or fluorine.

7. The device according to claim 1, wherein the liquid crystal material has positive dielectric anisotropy in the specific liquid crystal phase.

8. The device according to claim 1, wherein the device further comprises (i) a heating device configured to heat the liquid crystal material to the temperature at which the specific liquid crystal phase is developed, or (ii) a cooling device configured to cool the liquid crystal material to the temperature at which the specific liquid crystal phase is developed.

9. The device according to claim 6, wherein the device further comprises (i) a heating device configured to heat the liquid crystal material to the temperature at which the specific liquid crystal phase is developed, or (ii) a cooling device configured to cool the liquid crystal material to the temperature at which the specific liquid crystal phase is developed.

10. The device according to claim 8, wherein the liquid crystal material comprises 80% by weight or more, based on the weight of the liquid crystal material, of a compound described below:

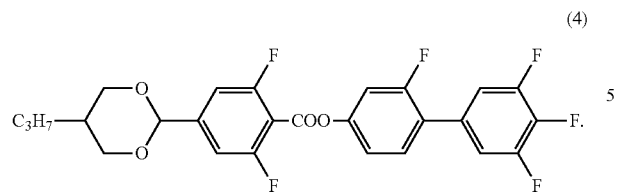
(4)
11. The device according to claim 9, wherein the liquid crystal material comprises 80% by weight or more, based on the weight of the liquid crystal material, of a compound described below:
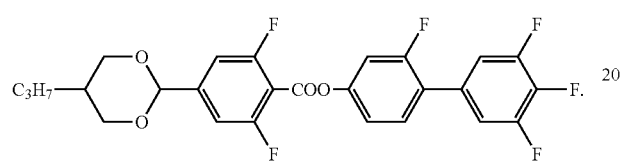
(4)
* * * * *